United States Patent
Bukowski et al.

[11] Patent Number: 6,149,429
[45] Date of Patent: Nov. 21, 2000

[54] DENTAL HANDPIECE SYRINGE ADAPTOR AND TIP

[76] Inventors: Joseph S. Bukowski, 33 Packanack Lake Rd.; Bruce S. Fine, 33 Wheeler Rd., both of Wayne, N.J. 07470

[21] Appl. No.: 09/272,997

[22] Filed: Mar. 19, 1999

Related U.S. Application Data

[63] Continuation-in-part of application No. 09/205,682, Dec. 4, 1998, abandoned.

[51] Int. Cl.[7] .................................................. A61C 17/00
[52] U.S. Cl. ............................................................ 433/80
[58] Field of Search ............................... 433/80, 81, 84, 433/85, 88, 89

[56] References Cited

U.S. PATENT DOCUMENTS

| | | | |
|---|---|---|---|
| D. 352,354 | 11/1994 | Davis et al. ........................... D24/112 |
| 796,536 | 8/1905 | Schultz ...................................... 433/82 |
| 1,858,056 | 5/1932 | Pieper . | |
| 2,460,473 | 2/1949 | Smith . | |
| 2,560,915 | 7/1951 | Bamberger . | |
| 2,641,839 | 6/1953 | Black . | |
| 2,799,934 | 7/1957 | Kern ......................................... 433/82 |
| 3,502,072 | 3/1970 | Stillman . | |
| 3,511,235 | 5/1970 | Stram . | |
| 3,581,399 | 6/1971 | Dragan . | |
| 3,593,423 | 7/1971 | Jones et al. . | |
| 3,640,304 | 2/1972 | Fox et al. ................................ 137/315 |
| 3,698,088 | 10/1972 | Austin, Jr. . | |
| 3,727,310 | 4/1973 | Baker . | |
| 3,771,527 | 11/1973 | Ruisi . | |
| 3,838,937 | 10/1974 | Hawley .................................... 408/193 |
| 3,858,323 | 1/1975 | Flatland . | |
| 3,874,083 | 4/1975 | Buckley . | |
| 4,026,025 | 5/1977 | Hunt . | |
| 4,048,723 | 9/1977 | Thorup . | |
| 4,217,101 | 8/1980 | Loge ........................................ 433/126 |
| 4,248,589 | 2/1981 | Lewis ........................................ 433/80 |
| 4,304,552 | 12/1981 | Wright et al. ............................ 433/126 |
| 4,386,911 | 6/1983 | Maloney et al. ......................... 433/125 |
| 4,403,959 | 9/1983 | Hatakeyama ............................ 433/126 |
| 4,531,913 | 7/1985 | Taguchi ..................................... 433/80 |
| 4,534,734 | 8/1985 | Lares ........................................ 433/126 |
| 4,619,612 | 10/1986 | Weber et al. ............................. 433/80 |
| 4,648,871 | 3/1987 | Jacob ........................................ 604/149 |
| 4,671,259 | 6/1987 | Kirchner .................................... 433/80 |
| 4,680,026 | 7/1987 | Weightman et al. ..................... 433/84 |
| 4,784,649 | 11/1988 | Imonti et al. ............................ 604/240 |
| 4,834,653 | 5/1989 | Edwardson .............................. 433/122 |
| 4,950,160 | 8/1990 | Karst ......................................... 433/88 |
| 4,975,054 | 12/1990 | Esrock ...................................... 433/80 |
| 4,984,984 | 1/1991 | Esrock ...................................... 433/88 |
| 5,049,071 | 9/1991 | Davis et al. .............................. 433/80 |
| 5,165,952 | 11/1992 | Solomon et al. ....................... 604/265 |

(List continued on next page.)

*Primary Examiner*—John J. Wilson
*Attorney, Agent, or Firm*—John N. Bain; William Squire

[57] ABSTRACT

An adaptor for a dental syringe handpiece has a central bore forming two chambers one of which receives a disposable syringe tip and the other selectively applied pressurized water and/or air from the handpiece. The adapter in one embodiment has a shoulder in the central bore acting as a stop for the tip to form the two chambers. In another embodiment, a tube attached to the adaptor in the adaptor bore serves as a stop for the tip. In another embodiment the tube has a sharp edge which engages the tip in the adaptor bore. The tip is urged against the edge by a gripping member and nut as the nut is tightened over the adaptor. The tip has several embodiments wherein a central passageway is surrounded by a plurality of outer passageways, the outer passages being arranged in arrays on different diameter circles. The outer passageways may be of different diameters and shapes. In a further embodiment, the tip is axially positioned in the adaptor bore at different positions to form an air-water mixing chamber of variable volume which sets the spray from a fine to coarse stream wherein the coarse stream is mainly large water droplets and the fine stream is a mist of fine water droplets and air. In a further embodiment, an anti-microbial agent is added to the plastic material forming the adaptor and tip to minimize microbes in the dispensed fluid.

29 Claims, 4 Drawing Sheets

U.S. PATENT DOCUMENTS

| | | | |
|---|---|---|---|
| 5,192,206 | 3/1993 | Davis et al. | 433/80 |
| 5,236,356 | 8/1993 | Davis et al. | 433/80 |
| 5,306,146 | 4/1994 | Davis et al. | 433/80 |
| 5,342,195 | 8/1994 | Davis et al. | 433/80 |
| 5,344,411 | 9/1994 | Domb et al. | 604/265 |
| 5,460,619 | 10/1995 | Esrock | 433/80 |
| 5,489,205 | 2/1996 | Davis et al. | 433/80 |
| 5,658,144 | 8/1997 | Tinder et al. | 433/80 |
| 5,772,433 | 6/1998 | Esrock | 433/80 |
| 5,825,958 | 10/1998 | Gollihar et al. | 606/15 |
| 5,941,702 | 8/1999 | Sharp et al. | 433/88 |

DENTAL HANDPIECE SYRINGE ADAPTOR AND TIP

This is a continuation-in-part application of application Ser. No. 09/205,682 filed Dec. 4, 1998, now abandoned.

This invention relates to dental handpiece syringes and adaptors and tips therefor for dispensing pressurized air, water or atomized air and water.

Various dental handpiece syringes are in wide use. Such syringes selectively dispense pressurized water streams, pressurized air streams or atomized water-air streams. One control button on the handpiece dispenses the air, a second button dispenses water and simultaneous depression of both buttons dispenses both water and air to provide an atomized spray. Tips generally may be removable to allow sterilization when made of metal.

Recent improvements introduced thermoplastic one use disposable tips. For example, see U.S. Pat. Nos. 5,192,206, 5,306,146, 5,236,356 and related patents which disclose syringe tips and adaptors therefor. These patents disclose that the tips can also be used as retractors as well as being disposable. These patents also disclose that it is important to separate the air and water entering into the syringe tip to avoid mixing. Separate channels are provided in the tip and adaptor coupled to corresponding channels in the handpiece supplying the water and air.

The present inventors recognize that there is no need to separate the water and air prior to the tip and adaptor and that mixing the air and water in the adaptor does not deleteriously affect the end operation. Since separate controls selectively dispense water or air, it is recognized that it does not matter if the fluids engage the same channels in the adaptor since they are dispensed separately from the handpiece.

A dental handpiece syringe adaptor and tip assembly according to the present invention comprises an adaptor for the handpiece having a chamber for receiving both air and water from the handpiece; and a dispensing tip secured to the adaptor in fluid communication with the chamber, the tip having at least one passageway for the fluid dispensed from the chamber.

In one aspect, the tip has a central through passageway and a plurality of offset through passageways, the passageways each in fluid communication with the chamber.

In a further aspect, a dental handpiece syringe adaptor is for attaching a fluid dispensing tip to the handpiece, the handpiece for providing pressurized air and water to the tip through the adaptor. The adaptor comprises an elongated body; the body having first and second ends and a cylindrical bore for receiving the tip at the first end; the body having first external peripheral threads adjacent to the second end for attaching the body to the handpiece and second external peripheral threads medially the first threads and first end for receiving a nut to secure the tip to the body; the body having a first passageway in the second end in fluid communication with the bore for supplying the water from the handpiece to the bore and a second passageway in the body in fluid communication with the bore for supplying air from the handpiece to the bore, the bore forming a first chamber for receiving the tip in spaced relation to the second end and a second chamber between the received tip and second end for receiving and mixing the supplied water and air.

In a further aspect, the adpator includes a stop in the bore for abutting the received tip at the interface of the first and second chambers.

In a further aspect, the first chamber has a larger diameter than the second chamber with a shoulder therebetween for forming a stop for the received tip.

In a further aspect, sealing means are provided for engagement with the second end and with the body periphery adjacent to the first threads for fluid sealing engagement with the handpiece to fluid isolate the first and second passageways from each other.

In a further aspect, a member secured to and extending from the second end in the bore second chamber forms the stop.

In a further aspect a nut is included having internal threads for attachment to the second external threads and having an end flange. Resilient means are between the end flange and the second end responsive to tightening of the nut on the adpator for clamping the tip to the adaptor.

In a further aspect, the member is a tube having a blunt end for abutting and locating the tip in the bore first chamber.

In a further aspect, the member has a relatively sharp edge for abutting and sealing engagement with the received tip.

In further aspect, a tip gripping member has resilient fingers located within the first chamber and responsive to tightening of the nut to the body second threads for gripping the received tip and for urging the gripped tip into the sealing engagement with the tube edge.

A dental handpiece syringe tip in a further aspect is for use with a handpiece for providing pressurized air and water to the tip through an adaptor. The tip comprises an elongated tubular member having first and second ends, the member having a first fluid receiving passageway extending for the length of the member and in fluid communication with the ends; and a plurality of second and a plurality of third fluid receiving passageways extending for the length of the member and in fluid communication with the ends, the second passageways lying on a circle of a first diameter and the third passageways lying on a circle of a second diameter different than the first diameter.

In a further aspect, the second passageways each have a diameter different than the diameter of the third passageways.

A dental handpiece syringe adaptor and tip assembly in a still further aspect comprises an adaptor for the handpiece having a chamber, the chamber having first and second passageways for receiving and mixing respective pressurized water and pressurized air received from the handpiece; a fluid dispensing tip in fluid communication with the chamber and having at least one fluid dispensing passageway and corresponding exit port for dispensing the mixed air and water; and means for adjustably setting the droplet size dispensed by the tip.

In a further aspect, the means for setting comprises a volume adjustment device associated with the chamber which adjustably sets the volume of the chamber.

The adjustment device may comprise means for settably locking the tip in the chamber at different positions in the chamber, the different positions corresponding to different chamber volumes.

Figures 1, 2:
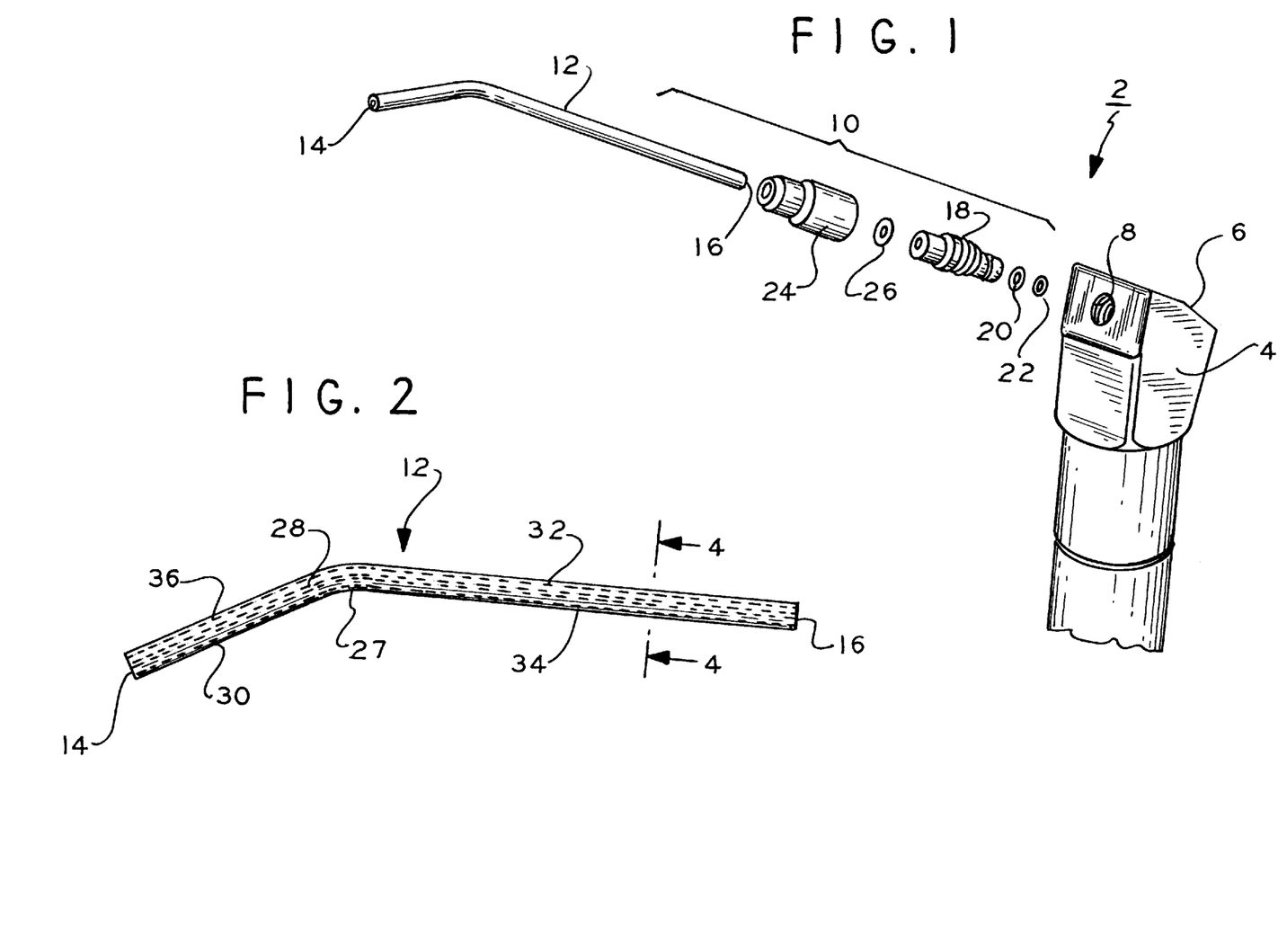
FIG. 1 is an exploded view of a dental syringe handpiece adaptor and tip according to an embodiment of the present invention
FIG. 2 is a side elevation view of the tip of FIG. 1.

In FIG. 1, syringe and handpiece assembly 2 comprises a conventional handpiece 4 for supplying pressurized water and air via separate conduits (not shown). Control buttons (not shown) on the handpiece operate a valve mechanism (not shown) for supplying the air and/or water. Each button may be operated individually or simultaneously with the other button to supply both the water and air simultaneously or individually. The handpiece 4 has a body 6 in which a threaded aperture 8 is formed. The air/water conduits are in communication with the aperture 8.

Syringe tip and adaptor assembly 10 comprises thermoplastic disposable one use tip 12 having opposing ends 14 and 16, an adaptor 18, O-rings 20 and 22 for sealing the adaptor 18 to the body 6 in the aperture 8, a nut 24 for attaching the tip 12 to the adaptor 18 and a sealing and clamping O-ring 26 responsive to the tightening of the nut 24 for clamping the tip 12 to the adpator 18.

Figure 4:
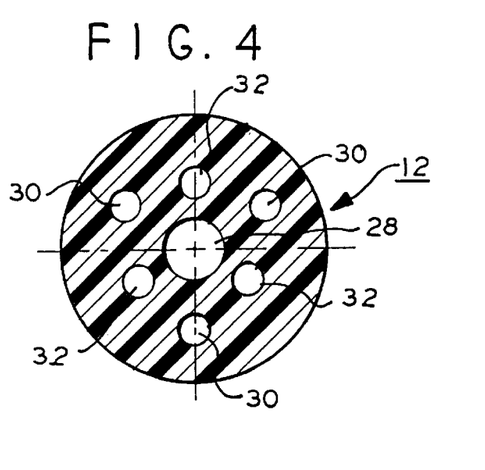
FIG. 4 is a sectional end elevation view of the tip of 2 taken along lines 4—4.

In FIGS. 2 and 4, the tip 12 is formed of extruded thermoplastic material preferably clear polycarbonate, cellulose acetate or equivalent tubing with a bend 27. Preferably, the tip is formed with a commercially available anti-microbial agent molded into the plastic material. Examples of anti-microbial agents include Medicoat® a polymer hybrid based on polyvinyl pyrrolidone and cellulose esters formulated in organic solvent solutions, Intersept® a synergistic blend of substituted ammonia salts of alkylated phosphoric acid admixed with free alkylated phosphoric acid, Silane® modified surfaces 3-(trimethoxysilyl) propyldimethyloctadecyl ammonium chloride or Boric Acid.

This agent is loaded into the plastic material during molding of the plastic tip. The agent is loaded in an amount and composition as known in the plastic pipe forming art, the anti-microbial agent being commercially available for use with plastic pipes. The agent is used in an effective amount, for example, preferably less than about 10% by volume and more preferably less than about 1%, to reduce bacteria in the fluid flowing in the plastic material cavity(s). The agent does not leach out of the material during use.

The tip may have a diameter of about 0.150 inches. The tip 12 has a relatively large central passageway 28 preferably of about 0.035 inches diameter and a plurality of a first array of relatively smaller passageways 30 lying on a first circle of about 0.0932 inches diameter in this embodiment and a second array of relatively smaller passageways 32 lying on a smaller circle of about 0.072 inches in diameter. The passageways 30 and 32 in this embodiment are of the same diameter of about 0.014 inches, there being three passageways each of passageways 30 and 32. The tip may have a longer length 34 of about 2 inches and a shorter length 36 of about one inch. The bend 27 is preferably formed by cold bending the tube.

Figure 5:
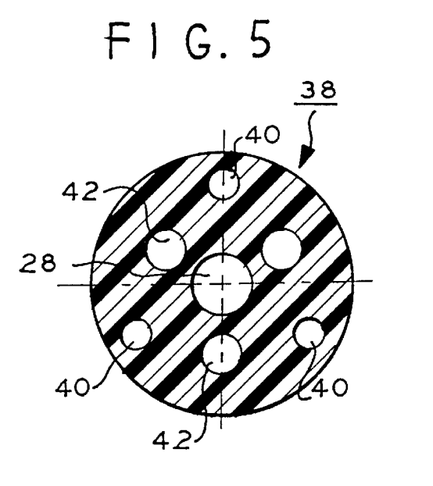
FIGS. 5–7 are end sectional elevation views of tips according to further embodiments of the present invention.
Figure 6:
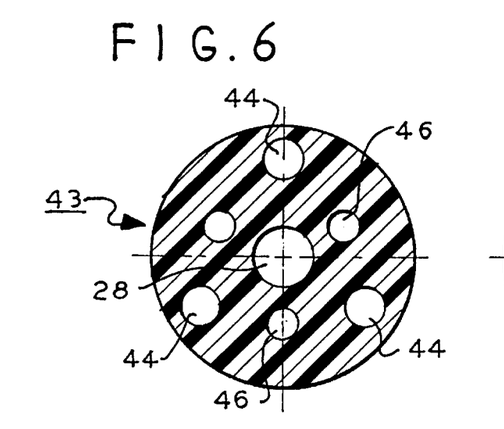

FIG. 5 shows a second embodiment of a tip 38 having a central passageway 28 and an array of smaller diameter passageways 40 and 42. Passageways 40 in the outer larger circle are smaller in diameter than passageways 42 in the inner smaller circle. In FIG. 6, in another embodiment, the larger passageways 44 in tip 43 are in the outer larger circle and the smaller passageways 46 are in the inner smaller circle. The larger passageways 42 and 44 may be of the same size and the smaller passageways 42 and 46 may be of the same size in each embodiment. The passageways 40 and 42 may be about 0.014 and 0.016 inches in diameter respectively, for example. Preferably, in all embodiments, the ends 14 and 16 of the tip 12 and so on are all heat polished to a smooth finish. All of the passageways extend for the entire length of the tips in communication with both tip ends. The tip 12 is preferably of uniform diameter or transverse dimension throughout as are the passageways therein.

Figure 3:
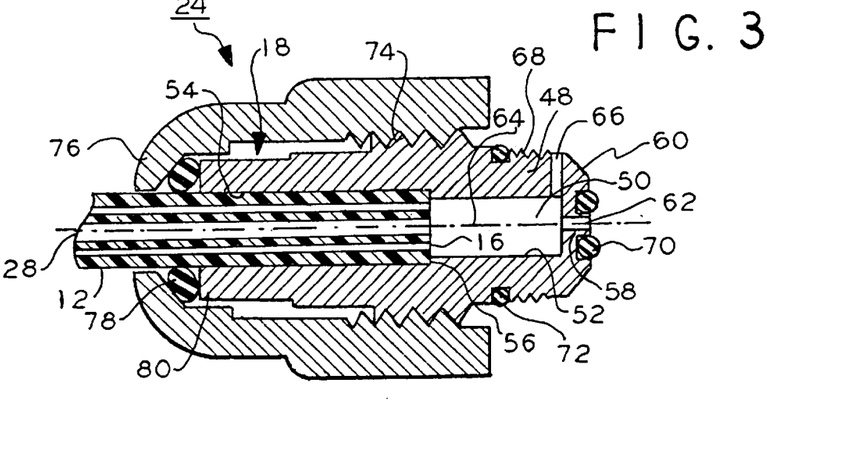
FIG. 3 is a side sectional elevation view of an adpator employed in the embodiment of FIG. 1.

In FIG. 3, adaptor 18 comprises a generally cylindrical body 48 having an axially extending bore 50. The adaptor may be metal or molded thermoplastic material. If molded thermoplastic material, it preferably is loaded with the anti-microbial agent noted above in an effective amount to reduce bacteria in the fluid flowing in the adaptor. Bore 50 is formed into two chambers 52 and 54 of different diameters having an annular shoulder 56. Chamber 52 is enclosed at end 58 by an end portion 60. A passageway 62 is in end portion 60 in communication with chamber 52 and the exterior of the body 48 along the bore 50 axis 64. A radial through bore passageway 66 couples the external ambient atmosphere to the chamber 52. The passageway 62 is coupled to the water source in the handpiece 4, FIG. 1, and the passageway 66 is coupled to the air source in the handpiece 4. When the appropriate buttons are pressed, water flows into the chamber 52 through passageway 62 and/or air flows into the chamber 52 via passageway 66 from the handpiece 4. The water and air enter the chamber 52 simultaneously when both buttons are simultaneously pressed.

External threads 68 on the body 48 mate with the threads in the aperture 8, FIG. 1 in the handpiece body 6. O-ring 70 seals the passageway 62 to the handpiece body water conduit. O-ring 72 seals the air passageway 66 to the handpiece body air conduit. External threads 74 attach the body 48 to nut 24.

Nut 24 is a cylindrical tube-like member with a radially inwardly extending end flange 76. The nut 24 has internal threads that mate with the adaptor external threads 74. An O-ring 78 is between the flange 76 and the end 80 of the adpator body 48.

In operation, the adaptor 18 is attached to the aperture 8 of the handpiece body 6 via threads 68. The O-ring 72 seals the threads 68 to the body 6. The O-ring 70 seals the end portion 60 of the adaptor body 48 to the handpiece body 6. The water passageway 62 is in fluid isolation from the air passageway 66 and from the ambient atmosphere. This forms a relatively more permanently attachment of the adaptor 18 to the body 6 of the handpiece 4.

The disposable tip 12 is then attached to the adaptor 18. The tip 12 end 16 is inserted into the adaptor chamber 54 of the bore 50 until it abuts the shoulder 56. This spaces the tip 12 end 16 from the end portion 60 forming the chamber 52. The nut 24 is then tightened until the flange 76 squeezes the O-ring 78 against the tip 12 outer surface. This squeezing action distorts the O-ring 78 clamping it tightly against the tip releasably locking the tip to the adaptor. When it is desired to dispose of the tip 12 after use, the nut is loosened and the tip removed without disengaging the adaptor 18 from the handpiece body. Thus the O-rings 70 and 72 remain in place and are not subject to repetitive removal action and subsequent deterioration due to such removal of the adaptor 18 from the handpiece body. When the water button is operated, water flows into the chamber 52 and into at least the central passageway of the tip 12. Because the passageways 30 and 32 of the tip are relatively small, the water, due to its surface tension, may not flow into these passages. This is not important.

When air alone is supplied, it flows through all of the tip passageways. When both air and water are supplied to the chamber 52 they mix. The tip 12 thus forms the mixture into an atomized spray at the exit end 14. Because the passageways 30 and 32 are small, it is possible that only air enters these passages and water and air enters the central passageway 28. The mixed air and water forms the desired atomized spray exiting the tip. Thus no sealing is required to separate the air and water in an adaptor chamber as occurs in the patents mentioned in the introductory portion. The anti-microbial agent in the tip disinfects the fluids flowing therethrough.

Figure 8:
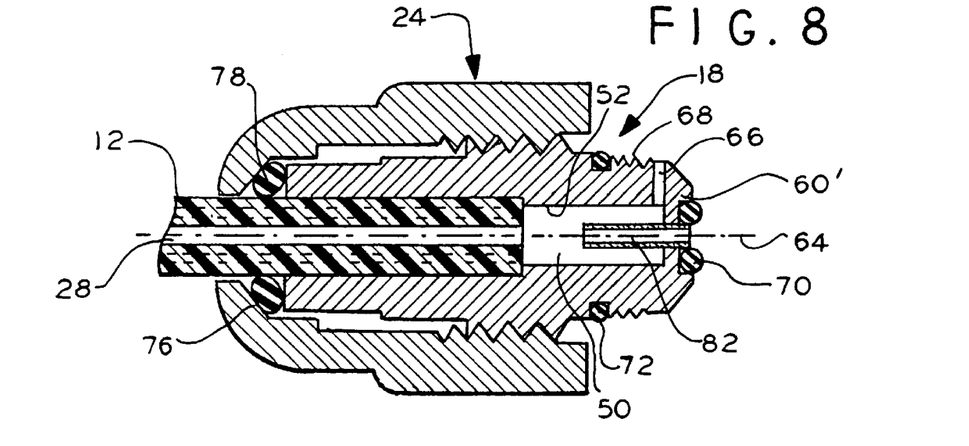
FIGS. 8–10 are side sectional elevation views of further embodiments of an adaptor according to the present invention.

In FIG. 8, the parts are substantially identical to the adapter and nut of FIG. 3 except the end portion 60' includes a tube 82 forming a water passageway therethrough. The tube 82 may be metal or plastic and extends through a bore in the end portion 60' on the axis 64. The tube 82 introduces water further into the chamber 52 away from the air inlet at passageway 66.

Figure 10:
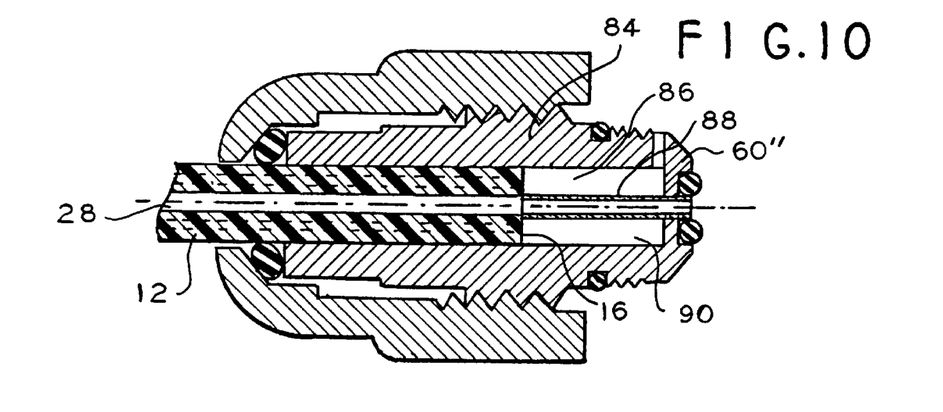

In FIG. 10, the adpator 84 bore 86 is of uniform diameter throughout. There is no shoulder in the bore 86 as in the embodiments of FIGS. 3 and 8. However, in this case tube 88 is in a bore in end portion 60" and extends for the full axial extent of the chamber 90 in the bore 86. Tip 12 is attached to the adaptor in the same way as in FIGS. 3 and 8. The tip 12 end 16 abuts the blunt end of the tube 88. The tube 88 thus serves as a stop forming the chamber 90, preventing the tip from being fully inserted into the bore 86. In this way, water flowing through the tube 88 flows directly into the passageway 28 of the tip 12. No need is provided for sealing the tip 12 end 16 to the tube 88. Thus, it is possible some water may flow into the chamber 90 or air into the tip bore 28.

Figure 9:
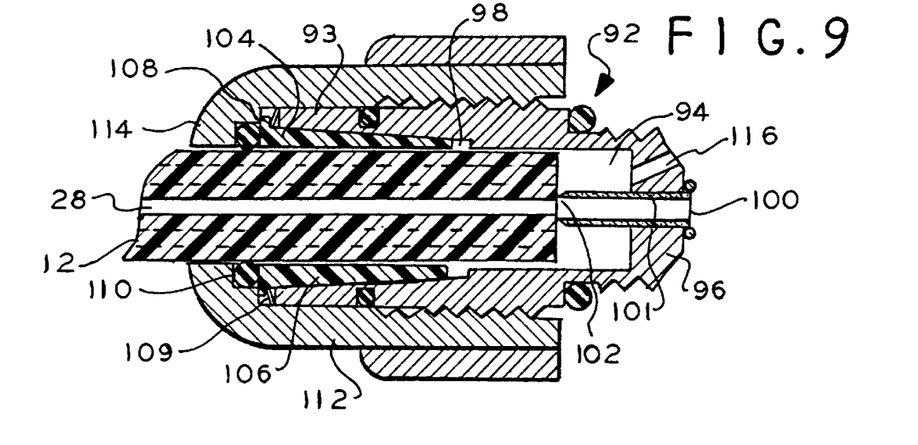

In FIG. 9, adaptor 92 comprises a body 93 which has a cylindrical bore 94 enclosed by an end wall 96. The bore 94 is in communication with a conical bore 98. A rigid tube 100 is in a bore 101 in the end wall 96. The tube 100 has a tapered end with a sharp edge 102 in bore 94 and forms a first chamber in the bore 94. The end edge 102 abuts and digs into the received tip 12 forming a seal therewith. The central passageway 28 of the tip 12 forms a continuous conduit with the bore of the tube 100 forming a water passageway for water flowing from the handpiece 4 in fluid isolation from the bore 94 chamber.

Tip gripping member 104 is employed to force the tip 12 into such sealing engagement with the tube. The member 104 has a plurality of axially extending cantilevered fingers 106 overlying the tip 12 in the adpator bore 98. The fingers form a complementary conical external surface for mating with the bore 98. The member 104 has a flange 108 which abuts O-ring 110. Flange 108 abuts a spring annular washer 109 at the interface between the gripping member flange 108 and the end edge of the adaptor 92 body 93. The nut 112 has a flange 114 which abuts O-ring 110.

When the nut 112 is tightened, it forces the O-ring 110 against the member 104 flange 108 in an axial direction toward the tube 100. The O-ring 110 is also squeezed and expands radially inwardly against the tip 12 gripping the tip and pulling it with the member 104 as the member 104 displaces axially to the right in the figure. This pulling of the tip 12 toward the tube 100 jams the tip 12 against the tube 100 sharp edge 102 forming a fluid tight seal therewith. Edge 102 is between the central passageway 28 and the smaller air passageways 32, FIG. 4. Thus the tube 100 isolates the air passageways of the tip 12 from the central water passageway. The tube 100 thus also forms a stop for the tip so that tip 12 does not fill the chamber 94 and block the air passageway 116. This embodiment is for those applications where it is desired to provide separate air and water paths in the tip when both water and air are applied.

Air is supplied to the chamber 94 via passageway 116 which is inclined to the adaptor longitudinal axis. This air flows into the tip 12 passageways 30 and 32 which are in communication with the chamber 94. However, water flowing in the tube 100 enters the tip central passageway 28, FIG. 4, without mixing with the air due to the fluid seal formed by edge 102 of the tube 100. Thus, air and water may be supplied to the tip in separate passageways without mixing in the tip. The air and water first mix at the tip exit end 14 forming an atomized spray.

Figure 7:
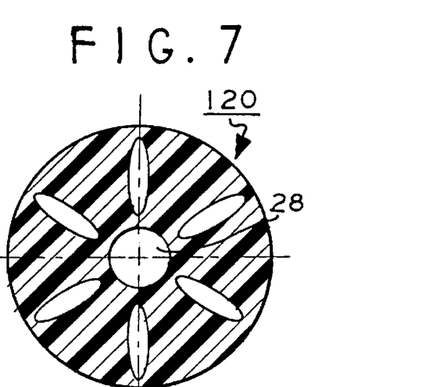

FIG. 7 shows another embodiment wherein the passageways 118 in the tip 120 are elliptical in shape if desired. The long elliptical axis is radial to provide increased air pressure if desired.

Figure 11:
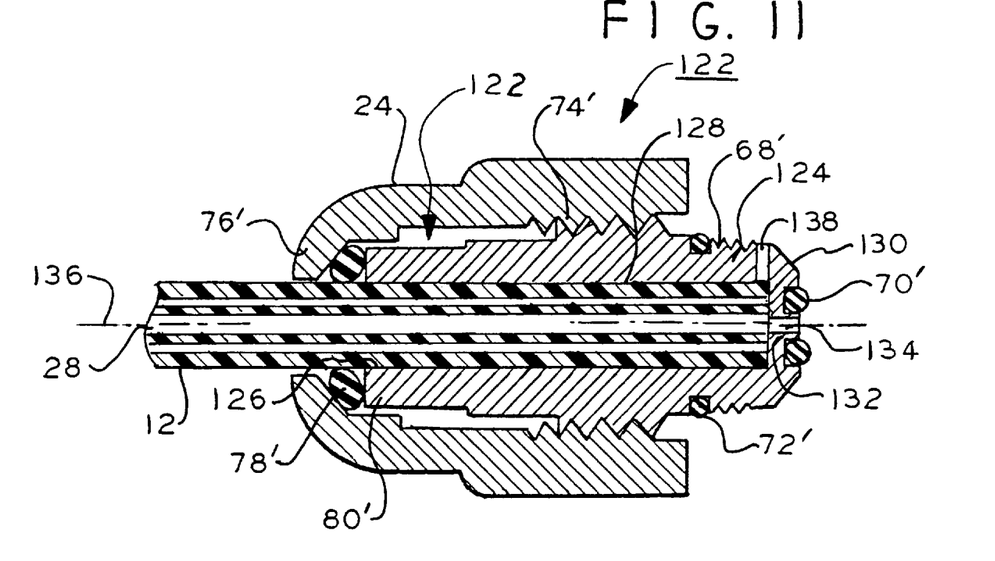
FIGS. 11 and 12 are side sectional elevation view of different stages of use of an Adaptor employed in a still further embodiment.

In FIG. 11, adaptor 122 comprises a generally cylindrical body 124 having an axially extending circular cylindrical bore 126. Bore 126 forms a chamber 128. Chamber 128 is enclosed at end 130 by an end portion 132. A passageway 134 is in end portion 132 in communication with chamber 128 and the exterior of the body 124 along the bore 126 axis 136. A radial through passageway slot 138 in the body 124 couples the external ambient atmosphere to the chamber 128. The slot extends in a plane normal to the plane drawing sheet. The passageway 134 is coupled to the water source in the handpiece 4, FIG. 1, and the passageway slot 138 is coupled to the air source in the handpiece 4. When the appropriate buttons are pressed, water flows into the chamber 128 through passageway 134 and/or air flows into the chamber 128 via passageway slot 138 from the handpiece 4. The water and air enter the chamber 128 simultaneously when both buttons are simultaneously pressed.

External threads on the body 124 mate with the threads in the aperture 8, FIG. 1 in the handpiece body 6. The remaining components with primed reference numerals are identical to the components in FIG. 3 without the primes. However, the O-ring 70' is optional and preferably is omitted in a further embodiment (not shown). In this case the end face of end portion 132 does not have an O-ring groove but is flat through out. Further, slot 138 may be replace with a bore (not shown) in end portion 132 end 130 in the chamfer surface of end 130 normal to this surface. This bore is thus inclined to the axis 136 at a complementary angle to the inclination of the end 130 chamfered surface. The O-ring may be omitted because there is no need to separate the air and water which are mixed as described above in chamber 128 regardless the presence of such an O-ring, which is superfluous.

In operation, tip 12 is inserted into bore 126. Tightening of the nut 24 clamps the O-ring 78' between the body 124 end surface at end 80' and nut 24 flange 76'. This clamps the tip 12 to the body 124 in the axial position along axis 136. In FIG. 11, the tip end 16 abuts the end portion 132 of the body 124. Water flows through the passageway 134 directly into the tip 12 passageway 28. Pressurized air in slot 138 may enter into the tip 12 passageways 30 and 32 via chamber 128 formed by bore 126. The air may also combine with the water in the water passageway 28. This is acceptable. This forms a relative strong stream of water in passageway 28. The pressurized air primarily enters the passageways 30 and 32 due to seepage. The combined air and water at the tip discharge end of the passageways 28, 30 and 32 forms a relatively fine spray of water droplets at the exit ports.

Figure 12:
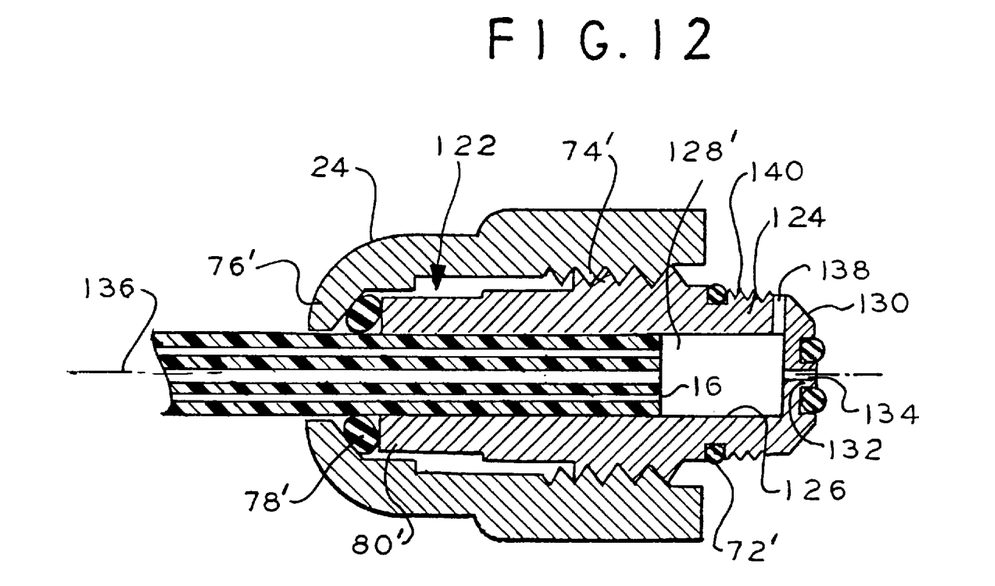

In FIG. 12, the tip 12 end 16 in this embodiment, is spaced from the end portion 132 forming an end chamber 128' between the tip end 16 and end portion 132. Chamber 128' forms a water-air mixing chamber to form a more coarsely atomized spray of the fluids. The tip end 16 may be variably set to any axial position along the axis 136 to set the volume of the chamber 126. The further the tip 12 end 16 is spaced from the end portion 132, the larger the chamber 128' and the coarser the spray droplets, i.e., the droplets become larger, at the tip 12 fluid discharge ports. Thus, the axial position of the tip 12 along axis 136 can adjustably set the spray from a fine mist to a coarse stream as desired. The parameters, coarse to fine water droplet sizes, of the stream are thus set according to the axial position of the tip end 16 relative tot the end portion 132, i.e., by setting the relative size of the volume of the water-air mixing chamber 128'. The tip 12 can be manually set to any axial position as desired along the axis 136 in the bore 126 to set the spray parameters. The tip 12 is then clamped in place accordingly by tightening the nut 24.

While the tip 12 is used to adjust the mixing chamber volume, other devices may be so employed. For example, the end portion 132 may be adjustably attached to the body 124 by threads (not shown). The tip may have a fixed position as set by the shoulder 56, FIG. 3. The axial position of the end portion 132 is then adjustably set to adjust the volume of the chamber 126, FIG. 11. It should be understood that in the end position of the tip, FIG. 11, while abutting the end portion 132 and closely engaged in the bore 126, still permits some mixing of the air and water due to seepage of pressurized air from the slot 138 into the outer passageways 30 and 32 and to a lesser extent to the central passage 28 of the tip 12 due to the lack of sealing and imperfect fit of the parts at this location. Thus there is some mixing of air and water at this position. But due to the relatively large volume of water in the central passageway 28 and the relatively large volume of air entering the air passageways 30 and 32 of the tip 12 due to pressurized air seepage, the droplets are relatively small creating a fine mist at the tip discharge as in conventional tips.

A still other adjustment device for adjusting the volume size may include a plunger (not shown) in the side wall of the adapter which adjustably sets the volume of the chamber 126 and which may also include a tube (not shown) for coupling the tip to the passageway 134, FIG. 12. The tube may be transversely adjustably set on and off the axis 136.

It will occur to one of ordinary skill that various modifications may be made to the disclosed embodiments which are given by way of example and not limitation. It is intended that the scope of the invention be defined by the appended claims.

What is claimed is:

1. A dental handpiece syringe adaptor for attaching a fluid dispensing tip to the handpiece, the handpiece for providing pressurized air and water to the tip through the adaptor, the adaptor comprising:

an elongated body;

said body having first and second ends and a cylindrical bore for receiving said tip at the first end;

said body having first external peripheral threads adjacent to the second end for attaching the body to said handpiece and second external peripheral threads medially the first threads and first end for receiving a nut to secure the tip to said body;

the body having a first passageway in said second end in fluid communication with the bore for supplying said water from said handpiece to the bore and a second passageway in the body in fluid communication with the bore for supplying air from said handpiece to the bore, said bore forming a first chamber for receiving the tip in spaced relation to said second end and a second chamber between the received tip and second end for receiving and mixing said supplied water and air; the first chamber having a larger diameter than the second chamber with a shoulder therebetween for forming a stop for said received tip.

2. The adaptor of claim 1 including a stop in said bore for abutting the received tip at the interface of said first and second chambers.

3. The adaptor of claim 2 including a member secured to and extending from said second end in the bore second chamber for forming said stop.

4. The adaptor of claim 3 wherein the member is a tube having a blunt end for abutting and locating said tip in said bore first chamber to minimize said mixing in said second chamber.

5. The adaptor of claim 1 including sealing means for engagement with the second end and with the body periphery adjacent to the first threads for fluid sealing engagement with the handpiece to fluid isolate the first and second passageways from each other.

6. The adaptor of claim 1 further including said nut having internal threads for attachment to said second external threads and an end flange, and resilient means between said end flange and said second end responsive to tightening of the nut on said adpator for clamping the tip to said adaptor.

7. A dental handpiece syringe tip, the handpiece for providing pressurized air and water to the tip through an adaptor, the tip comprising:

an elongated tubular member having first and second ends, the member having a first fluid receiving passageway extending for the length of the member and in fluid communication with said ends; and a plurality of second and a plurality of third fluid receiving passageways extending for the length of the member and in fluid communication with said ends, the second passageways lying on a circle of a first diameter and the third passageways lying on a circle of a second diameter different than the first diameter.

8. The tip of claim 7 wherein the second passageways have a diameter different than the diameter of the third passageways.

9. The tip of claim 7 wherein the second passageways have a diameter less than the diameter of the third passageways.

10. The tip of claim 7 wherein second passageways have a diameter greater than the diameter of the third passageways.

11. A dental handpiece syringe adaptor and tip assembly for attaching a fluid dispensing tip to the handpiece, the handpiece for providing pressurized air and water to the tip through the adaptor, the assembly comprising:

an adaptor comprising:
an elongated body;
said body having first and second ends and a cylindrical bore for receiving said tip at the first end;
said body having first external peripheral threads adjacent to the second end for attaching the body to said handpiece and second external peripheral threads medially the first threads and first end for receiving a nut to secure the tip to said body;

the body having a first passageway in said second end in fluid communication with the bore for supplying pressurized water from said handpiece to the bore and a second passageway in the body in fluid communication with the bore for supplying pressurized air from said handpiece to the bore, said bore having a first chamber for receiving the tip and a second chamber between the received tip and second end for receiving and mixing said supplied water and air; and a tip attached to the adaptor in said first chamber and spaced from said second end by said second chamber; said tip comprising:

an elongated tubular member having third and fourth ends, the member having a first fluid receiving passageway extending for the length of the member and in fluid communication with said third and fourth ends; and a plurality of second and a plurality of third fluid receiving passageways extending for the length of the member and in fluid communication with said tip ends;

the second passageways lying on a circle of a first diameter and the third passageways lying on a circle of a second diameter different than the first diameter.

12. The assembly of claim 11 including a stop in said bore for abutting the received tip at the interface of said first and second chambers.

13. The assembly of claim 12 including a member secured to and extending from said second end in the bore second chamber for forming said stop.

14. The assembly of claim 11 wherein the first chamber has a larger diameter than the second chamber with a shoulder therebetween for forming a stop for said received tip.

15. The assembly of claim 11 including sealing means for engagement with the second end and with the body periphery adjacent to the first threads for fluid sealing engagement with the handpiece to fluid isolate the first and second passageways from each other.

16. The assembly of claim 11 further including said nut having internal threads for attachment to said second external threads and an end flange, and resilient means between said end flange and said second end responsive to tightening of the nut on said adpator for clamping the tip to said adaptor.

17. A dental handpiece syringe adaptor and tip assembly comprising:

an adaptor for the handpiece having a chamber, the chamber having first and second passageways for receiving and mixing respective pressurized water and pressurized air received from the handpiece;

a fluid dispensing tip in fluid communication with the chamber and having at least one fluid dispensing passageway and corresponding exit port for dispensing the mixed air and water; and means for adjustably setting the droplet size dispensed by the tip.

18. The assembly of claim 17 wherein the means for setting comprises a volume adjustment device associated with the chamber which adjustably sets the volume of the chamber.

19. The assembly of claim 17 wherein the means for setting the droplet size comprises means for settably locking the tip in the chamber at different positions in the chamber.

20. The assembly of claim 19 wherein the chamber is formed by an axially extending bore in the adaptor for axially receiving the tip, the axial position of the tip for setting the chamber and droplet size and clamp means for locking the tip to the adaptor in the set axial position.

21. The assembly of claim 20 wherein the tip is movably secured in the chamber in a position so that the at least one tip passageway directly receives the water from the water receiving passageway wherein the size of the chamber is at a minimum.

22. The assembly of claim 17 wherein the chamber is arranged for selectively mixing the received water and air and the means for adjusting include arranging the tip position in the chamber so that the water and air exhibit a settable droplet size.

23. A dental handpiece syringe adaptor and tip assembly comprising:

an adaptor for the handpiece having a chamber, the chamber having first and second passageways for receiving and mixing respective pressurized water and pressurized air received from the handpiece;

a fluid dispensing tip in fluid communication with the chamber and having at least one fluid dispensing passageway and corresponding exit port for dispensing the mixed air and water;

at least one of the tip and adaptor comprising thermoplastic material including an anti-microbial agent embedded in the material for minimizing microbes in the dispensed mixed air and water.

24. The handpiece of claim 23 wherein the anti-microbial agent comprises any one of the group comprising a polymer hybrid based on polyvinyl pyrrolidone and cellulose esters formulated in organic solvent solutions, a synergistic blend of substituted ammonia salts of alkylated phosphoric acid admixed with free alkylated phosphoric acid, modified surfaces 3-(trimethoxysilyl) propyldimethyloctadecyl ammonium chloride and Boric Acid.

25. A dental handpiece syringe adaptor for attaching a fluid dispensing tip to the handpiece, the handpiece for providing pressurized air and water to the tip through the adaptor, the adaptor comprising:

an elongated body;

said body having first and second ends and a cylindrical bore for receiving said tip at the first end;

said body having first external peripheral threads adjacent to the second end for attaching the body to said handpiece and second external peripheral threads medially the first threads and first end for receiving a nut to secure the tip to said body;

the body having a first passageway in said second end in fluid communication with the bore for supplying said water from said handpiece to the bore and a second passageway in the body in fluid communication with the bore for supplying air from said handpiece to the bore, said bore forming a first chamber for receiving the tip in spaced relation to said second end and a second chamber between the received tip and second end;

a stop in said bore for abutting the received tip at the interface of said first and second chambers; and a member secured to and extending from said second end in the bore second chamber for forming said stop;

the member comprising a tube with a relatively sharp edge for abutting and sealing engagement with said received tip to preclude mixing of air and water in said second chamber to provide water and air to said tip in separate paths.

26. The adaptor of claim 25 further including a tip gripping member having resilient fingers located within the first chamber and responsive to tightening of the nut to the body second threads for gripping the received tip and for urging the gripped tip into said sealing engagement with said tube edge.

27. A dental handpiece syringe adaptor and tip assembly for attaching a fluid dispensing tip to the handpiece, the handpiece for providing pressurized air and water to the tip through the adaptor, the assembly comprising:

an adaptor comprising:
  an elongated body;
  said body having first and second ends and a cylindrical bore for receiving said tip at the first end;
  said body having first external peripheral threads adjacent to the second end for attaching the body to said handpiece and second external peripheral threads medially the first threads and first end for receiving a nut to secure the tip to said body;
  the body having a first passageway in said second end in fluid communication with the bore for supplying pressurized water from said handpiece to the bore and a second passageway in the body in fluid communication with the bore for supplying pressurized air from said handpiece to the bore, said bore having a first chamber for receiving the tip and a second chamber between the received tip and second end for receiving and mixing said supplied water and air;
a tip attached to the adaptor in said first chamber and spaced from said second end by said second chamber; and
a stop in said bore for abutting the received tip at the interface of said first and second chambers, said stop being formed by a member secured to and extending from said second end in the bore second chamber.

28. A dental handpiece syringe adaptor and tip assembly comprising:

an adaptor for the handpiece having a chamber for receiving both air and water from the handpiece; and
a dispensing tip secured to the adaptor in fluid communication with the chamber, said tip having at least one passageway for the fluid dispensed from the chamber;
the tip comprising plastic material and being molded with an anti-microbial agent in the plastic material which agent is in fluid communication with the at least one tip passageway for reducing microbes in fluid flowing in the at least one passageway.

29. A dental handpiece syringe adaptor and tip assembly comprising:

an adaptor for the handpiece having a chamber for receiving both air and water from the handpiece; and
a dispensing tip secured to the adaptor in fluid communication with the chamber, said tip having at least one passageway for the fluid dispensed from the chamber;
the adaptor being molded of thermoplastic material and being molded with an anti-microbial agent in the plastic material which agent is in fluid communication with the chamber for reducing microbes in fluid flowing in the chamber.

* * * * *